(12) United States Patent
Johnston

(10) Patent No.: US 9,131,670 B2
(45) Date of Patent: Sep. 15, 2015

(54) METHOD AND DEVICE FOR ATTRACTING AND COLLECTING EARTHWORMS

(71) Applicant: Duke Johnston, Landenberg, PA (US)

(72) Inventor: Duke Johnston, Landenberg, PA (US)

(73) Assignee: Duke Johnston, Landenberg, PA (US)

( * ) Notice: Subject to any disclaimer, the term of this patent is extended or adjusted under 35 U.S.C. 154(b) by 0 days.

(21) Appl. No.: 13/860,594

(22) Filed: Apr. 11, 2013

(65) Prior Publication Data

US 2013/0269616 A1   Oct. 17, 2013

Related U.S. Application Data

(60) Provisional application No. 61/623,638, filed on Apr. 13, 2012.

(51) Int. Cl.
```
A01K 29/00    (2006.01)
A01K 67/033   (2006.01)
A01K 97/04    (2006.01)
A01M 29/22    (2011.01)
```

(52) U.S. Cl.
CPC ............ *A01K 67/0332* (2013.01); *A01K 97/04* (2013.01); *A01M 29/22* (2013.01)

(58) Field of Classification Search
CPC ............ A01K 67/0332; A01K 97/04; A01M 2200/011; A01M 29/22
USPC .......................................... 119/6.7; 43/132.1
See application file for complete search history.

(56) References Cited

U.S. PATENT DOCUMENTS

| | | | | |
|---|---|---|---|---|
| 1,484,777 A * | 2/1924 | Hassenpflug | ................. | 84/422.4 |
| 2,642,699 A * | 6/1953 | Green | ........................... | 446/397 |
| 2,770,075 A * | 11/1956 | Moore | ............................... | 47/1.3 |
| 2,777,454 A * | 1/1957 | Kramer | ........................... | 135/87 |
| 3,139,087 A | 6/1964 | Liberatore | | |
| 3,455,049 A * | 7/1969 | Dyer et al. | ..................... | 446/102 |
| 3,898,756 A * | 8/1975 | Tolle | ............................... | 43/21.2 |
| 3,973,354 A | 8/1976 | Schommer | | |
| 4,114,762 A | 9/1978 | Beal et al. | | |
| 4,147,256 A | 4/1979 | Kiss | | |
| 4,187,946 A | 2/1980 | Stevenson | | |
| 4,556,679 A | 12/1985 | Koehler | | |
| 4,673,372 A * | 6/1987 | Hall | .............................. | 446/239 |
| 5,019,008 A * | 5/1991 | Hughes | ......................... | 446/207 |
| 5,447,088 A * | 9/1995 | Mester | ......................... | 84/422.4 |
| 5,775,352 A | 7/1998 | Obitts | | |
| 6,069,308 A * | 5/2000 | Rabb | ............................ | 84/422.4 |
| 7,766,022 B2 * | 8/2010 | Livacich et al. | ................ | 135/95 |
| 7,971,387 B2 | 7/2011 | Huddleston | | |
| 8,020,339 B1 | 9/2011 | Carter | | |
| 8,028,465 B1 | 10/2011 | Wuensch et al. | | |
| 8,079,173 B2 | 12/2011 | Corbitt | | |
| 2006/0042156 A1 * | 3/2006 | Holland | ....................... | 43/132.1 |
| 2007/0220750 A1 * | 9/2007 | Chen | .................................. | 30/1 |

FOREIGN PATENT DOCUMENTS

CA         2210186     *  7/1997  ............. A01M 1/02

* cited by examiner

Primary Examiner — Rob Swiatek
Assistant Examiner — Ebony Evans
(74) Attorney, Agent, or Firm — Joseph F. Aceto, Esq.

(57) ABSTRACT

An earthworm collecting device that is highly effective in causing earthworms to surface from their holes during the day time or at night and come to the surface. The device generates a rasping noise and a series of vibrations that resonate through the ground. These resonating vibrations cause the earthworms to surface which then allows for easy and rapid collection.

17 Claims, 7 Drawing Sheets

Storage mode having inner tube secured within outer tube

METHOD AND DEVICE FOR ATTRACTING AND COLLECTING EARTHWORMS

CROSS-REFERENCE TO RELATED APPLICATIONS

This application claims the benefit of U.S. Provisional Application No. 61/623,638, filed Apr. 13, 2012 and incorporated by reference in its entirety.

BACKGROUND OF THE INVENTION

1. Field of the Invention

This application relates generally to the procurement of earthworms for fishing bait, and has particular reference to an improved mechanical means that causes worms to leave their holes and come to the surface of the ground where they can easily be collected for use.

2. Description of the Prior Art

Devices for inducing earthworms to come out of the ground so that they can be collected for bait have been described. For example, compositions have been described which contain a substance that acts as a minor irritant to the worms, making them want to get above ground. Normally, the prepared composition is mixed with water and spread on the ground. As the soil absorbs the mixture, the worms begin to surface. An exemplary composition has been described in U.S. Pat. No. 4,556,679. Adding a chemical to the soil is not environmentally sound and may even damage the worms themselves.

Kiss (U.S. Pat. No. 4,147,256) describes a vibrational separator for harvesting worms living within a bedding apparatus using a frame and screen device which vibrates to separate the worms from their bedding material. Another harvester as described by Stevenson (U.S. Pat. No. 4,187,946) harvests worms from a trough-like bed with a digger that separates worms by raking the bedding pulling the worms toward a conveyor belt. However, both devices are expensive, not easily transported, and can't capture worms in their natural habitat or soil.

An electric worm collecting apparatus has also been described for capturing worms at the surface from soil electrically shocked (Schommer U.S. Pat. No. 3,973,354). The device consists of an electrical conducting rod having an end portion which is inserted into the ground. The rod generates an AC voltage that is channeled into the ground and surrounding soil, causing damage to the worms which may migrate to the surface.

A device is needed to collect earthworms from their natural environment using a simple and easy method that does not require preparation of caustic chemicals or the use of an elaborate apparatus, and yet is safe for the environment. The present invention embodies such a device and method using a portable vibrational device that sends sound waves through the ground to disturb the earthworms and force them to the surface for collection.

SUMMARY OF THE INVENTION

The present invention provides an improved earthworm collection device that is highly effective in causing worms to leave their holes and come to the surface in the day time or at night. A vibration or rasping noise is generated from a point source on the surface of the ground by holding the end of an applicator tube and placing the other end on the surface of the soil. A second striker tube is held perpendicular to the applicator with the other hand and rubbed or stroked back and forth across ribs or grooves spaced along the longitudinal axis of the applicator. The motion generates a rasping noise which is carried into the soil through contact by the end of the applicator. It is most effective in warm soil found in early spring through late fall when worms are more likely to migrate to the surface in response to vibration. One embodiment of the device consists of two hollow metal tubes, an inner applicator tube and outer striker tube. Another embodiment of the device consists of two solid 1 inch hardwood tubes for the applicator and striker. The series of ribbed or grooved indentations are located within a 10 inch area of the longitudinal axis of the applicator which then preferably tapers to a point at the end creating a tapered tip for contact approximately 6 inches below the surface of the soil. In the hollow metal tube embodiment, the outer, striker tube is slightly larger in diameter than the inner, applicator tube while the solid design has an applicator and striker with approximately the same diameter.

While not limiting the dimensions or composition of either tube, the inner tube preferably has a diameter of approximately ⅞ of an inch and the outer tube has diameter of approximately 1 inch. This allows the inner tube to slide inside the outer tube for easy storage or transport. The tubes can be made of steel, aluminum alloy, sturdy plastic, different types of wood, or any composition known in the art that would generate vibrations sufficient to cause the worms to surface. Both inner and outer tubes may optionally have a hand grip for easier use. The inner and outer tubes may optionally be threaded at their ends and screwed together for transport and storage. In the hardwood embodiment, the applicator and striker are both approximately 1 inch in diameter with the applicator having 0.75 width notches for optimum effect.

The device provides an easy and rapid means to collect earthworms from their natural environment for fishing or other uses. Because the device is portable and light, it can be carried to remote areas for worm collection. The device can be carried with fishing equipment for use during fishing trips when the supply of earthworm bait is low. A fishing kit is further claimed that is useful in remote locations or as a component in a tackle box.

DESCRIPTION OF THE PREFERRED EMBODIMENTS

Figure 1:
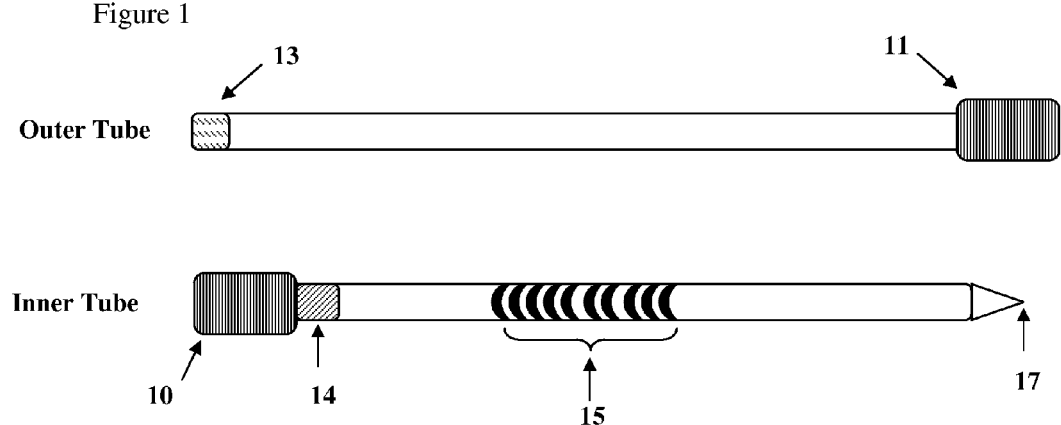
FIG. 1 is a diagram of the worm collecting device with inner and outer tubes.

Referring in detail to the drawings, the worm collecting device of the present invention consists of an outer and inner tube (see FIG. 1). Both structures are made from an elongated, hollow, and preferably metal tube. All metal compositions are considered such as, but not limited to, steel, aluminum alloy, or combinations thereof. A preferred composition is an aluminum alloy that is both sturdy and light weight. The tubes may also consist of sturdy plastic or a polymer design that can be forged into the shape of the tubes and withstand the physical interaction between the tubes which is needed to generate the vibrations necessary for worm migration. FIG. 1 depicts the outer tube which is used as a bow or striker against the inner tube. The outer tube contains a hand grip 11 at one end of the tube and female threads 13 at the opposite end. The inner tube contains a hand grip 10 on one end of the tube and a tube tip 17 for contact below the ground surface. Ribbed or grooved structures 15 along the middle section of the longitudinal axis of the inner tube provide an uneven surface so that when the outer tube is used as a bow and rubbed against the ribbed or grooved structures 15 of the inner tube, a vibration and rasping sound is generated through the inner tube. The ribbed or grooved structures considered in the present invention include evenly or unevenly spaced ribbed, pimpled, or combination ribbed/pimpled design rising above the surface along the center portion of the longitudinal axis of the inner tube. The present invention also considers grooved rings channeled into the surface of the inner tube and located along the center portion of the longitudinal axis. One embodiment consists of a series of channeled grooves spaced evenly or unevenly apart, but far enough apart so as to generate a rasping sound with vibrations that resonate through the inner tube and into the surface of the soil. Physical contact of the inner tube tip 17 below the ground surface can be used to generate sufficient vibrations for earthworm migration. The preferred length of the outer tube is approximately 26 inches with an outer diameter of the tube at approximately 1 inch. The preferred length of the inner tube is approximately 30 inches with an outer diameter of the tube at approximately ⅞ of an inch.

Another embodiment of the device consists of two solid wood tubes, an applicator and striker. While most any type of wood known is considered in the present invention, hardwood is a preferred type of wood. The applicator has a series of ribbed or grooved indentations along the length of the tube which tapers to a point at the end for penetration below with the soil. The striker is a comfortable length with approximately the same diameter as the applicator and is used for rubbing or stroking against the ribs or grooves of the applicator to generate a rasping noise which is carried under the soil surface through contact by the tip.

Figure 2:
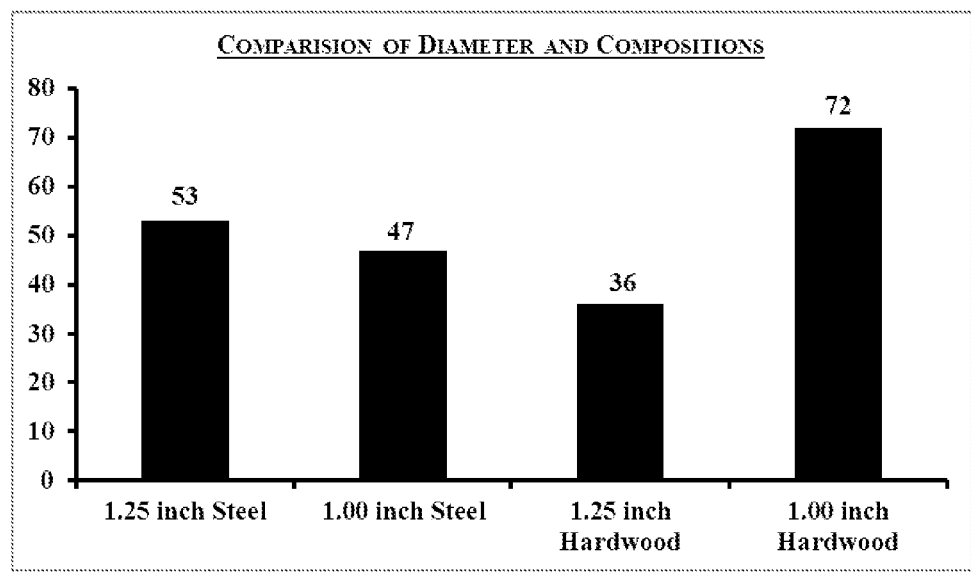
FIG. 2 is a bar graph showing the effectiveness of hardwood compared to steel using a 1 inch or 1.25 inch diameter represented as the number of worms collected.

While any diameter or composition capable of producing sound vibrations in the soil is considered in the present invention, a hardwood composition having a 1 inch diameter applicator and striker is most preferred in the present invention. FIG. 2 is a graphical representation comparing both steel and hardwood devices at 1 inch and 1.25 inch diameters. As shown in the figure, hardwood at 1 inch provides a better design over 1.25 inch for ease of use and attracting worms while steel provides good collection with virtually the same effect on worm collection between the 1 inch and 1.25 inch diameter steel design.

Figure 3:
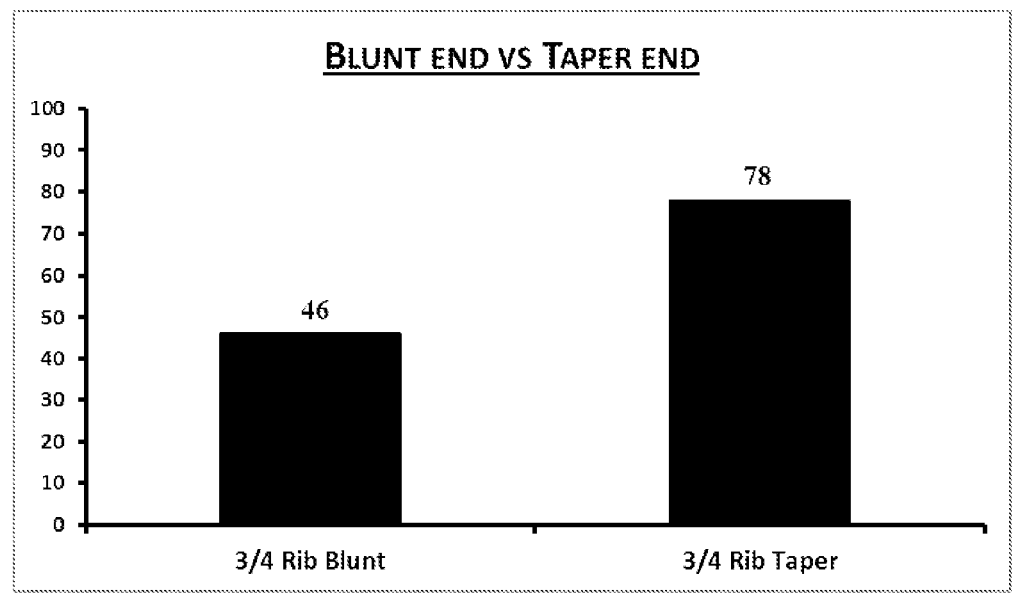
FIG. 3 is a bar graph showing the number of worms collected using a tapered hardwood applicator compared to a blunt-end hardwood applicator.

Another preferred embodiment is shown in FIG. 3. FIG. 3 shows the effect of a tapered tip at the end of the applicator compared to a similar applicator having a blunt end. A tapered tip, approximately 6 inches, is able to cause significantly more worms to surface.

Figure 4:
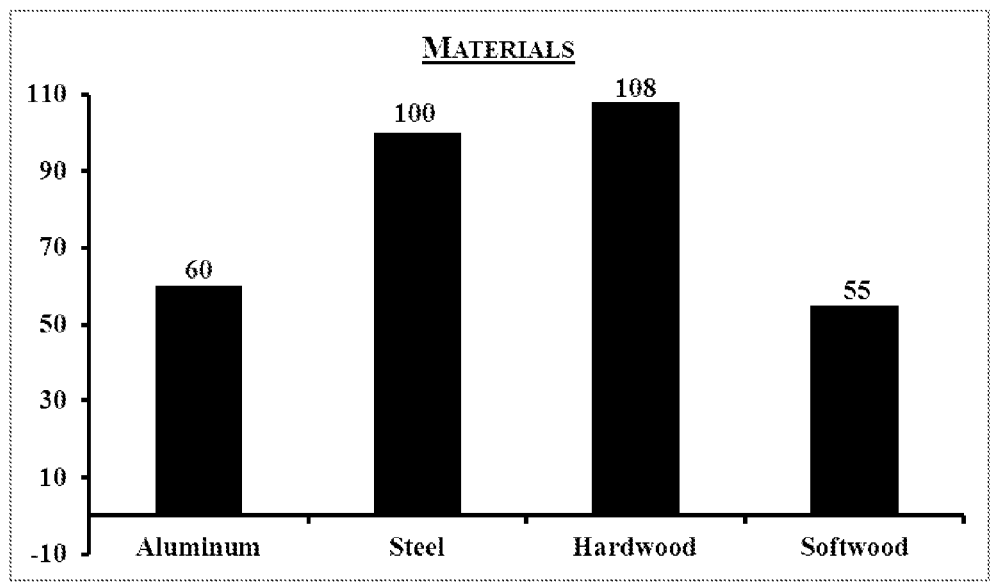
FIG. 4 is a bar graph representing the effect of different types of compositions on worm collection, shown are aluminum, steel, hardwood, and softwood.

While all composites capable of generating sound vibrations in soil are considered in the present invention, FIG. 4 shows differences in aluminum, steel, hardwood, and softwood compositions. A hardwood composition provides the most effective composition for getting the worms to surface and collect.

Figure 5:
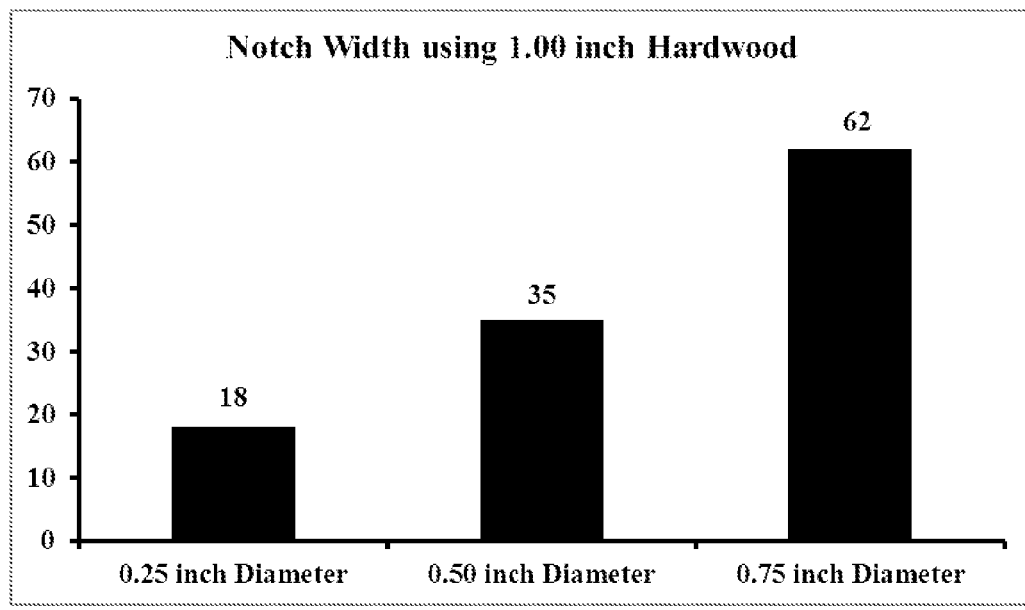
FIG. 5 is a bar graph comparing 0.25, 0.50, and 0.75 width notches in a 1 inch diameter applicator.

While the present invention considers any size notch width that provides optimum worm collection, FIG. 5 compares 0.25, 0.50, and 0.75 inch notches in a 1 inch applicator. The effect on worm surfacing and collection is most effective in a 1 inch applicator having 0.75 inch notches. Notches contained along the longitudinal axis of the applicator and within an approximate 10 inch area provide the optimum comfort and ease for striking.

Figure 6:
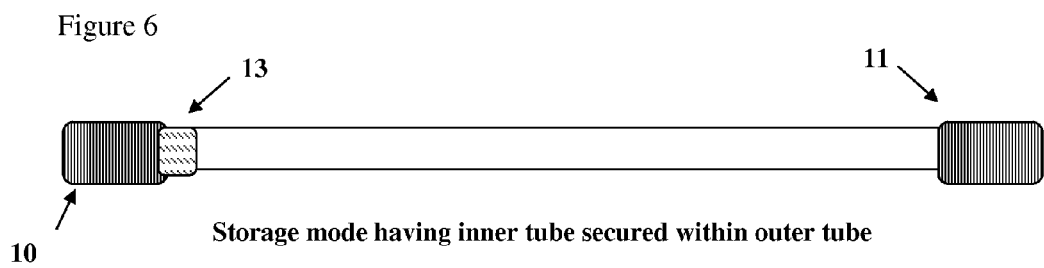
FIG. 6 shows one embodiment of the worm collecting device in storage or transport mode with the inner tube secured within the hollow of the outer tube.

In another embodiment incorporating the hollow tube design, the device can be interlocked for storage or transportation. Here, the female threads 13 of the outer, striker tube are threaded into the male threads 14 of the inner, applicator tube after insertion of the inner tube into the hollow of the outer tube. FIG. 6 shows the device in storage and transport mode. The inner tube is slightly smaller in both its length and diameter so that is can easily be inserted into the outer tube and then secured by threading the male threads 14 of the inner tube shown in FIG. 1 with the female threads 13 of the outer tubes. The resulting structure has the inner tube encased within the outer tube except for the hand grip 10 which remains exposed on the opposite end of hand grip 11 on the outer tube.

Figure 7:
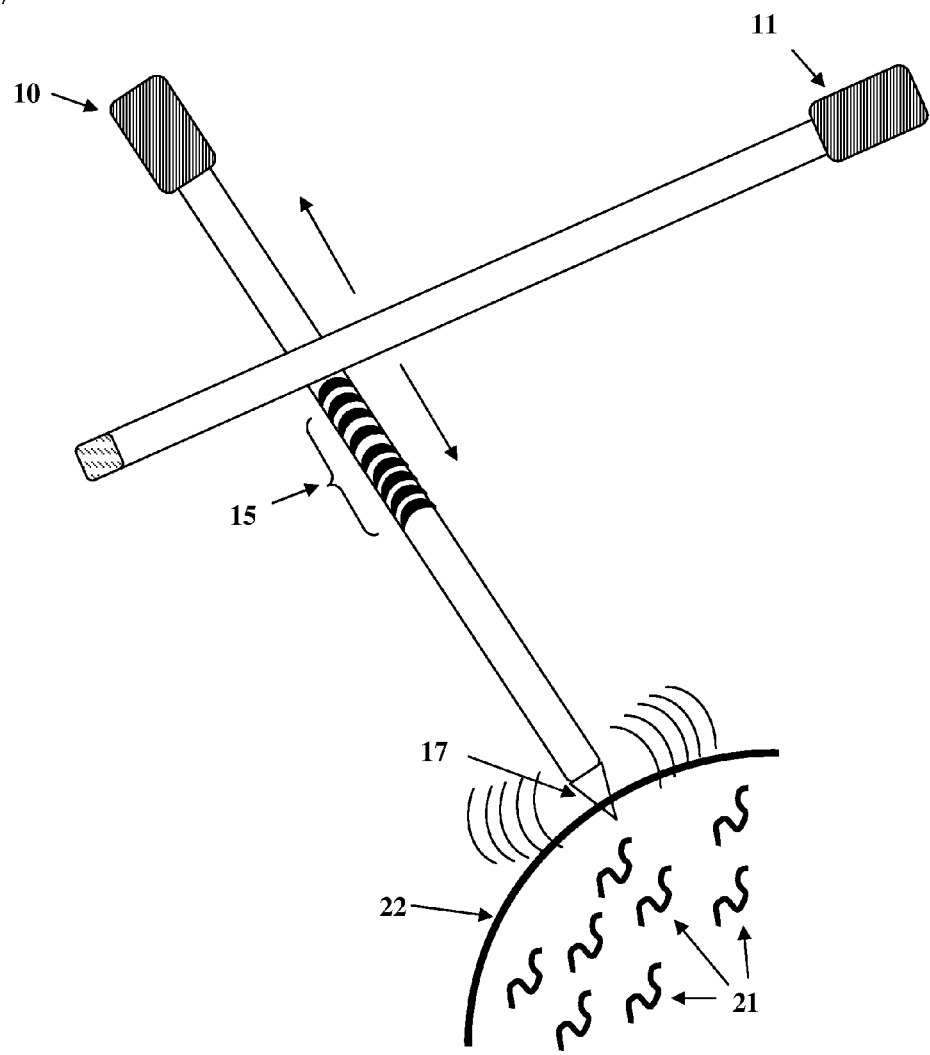
FIG. 7 is drawing showing the worm collecting device as it generates vibration to force the earthworms to the ground surface.

FIG. 7 is a schematic showing the device as it would be used for collecting earthworms either in the hollow metal tube embodiment or the solid hardwood embodiment. The applicator is grabbed at hand grip 10 and held upright with the tapered tip 17 under the surface of the ground 22 within an area where earthworms 21 are to be collected. The striker is then held by its hand grip 11 perpendicular to and against the notched, mid-sectional portion of the applicator and stroked along the longitudinal axis of the applicator, maintaining the striker in an approximately orthogonal orientation to the longitudinal axis of the inner tube and in such a manner as to provide a comfortable and even stroke for the average adult forearm. The striker is rubbed or stroked against the ribbed or grooved structures 15 while the applicator remains in contact below the surface of the soil 22 through tapered tip 17. Repetitive back-and-forth stroking motion using the striker across the ribbed or grooved structure 15 of the applicator eventually results in the surfacing of the earthworms 21. The number cycles and duration of the repetitive motion will vary depending upon the soil and environmental conditions. Most effective is approximately 40 strokes per 30 seconds, exerting about 2 pounds of pressure against the applicator with the striker. Once the earthworms have surfaced, they can be easily collected for use.

Although the present invention has been described with reference to specific embodiments, workers skilled in the art will recognize that many variations can be made therefrom. It is to be understood and appreciated that this discovery in accordance with this invention are only those which are illustrated of the many additional potential variations that can be envisioned by one of ordinary skill in the art, and thus are not in any way intended to be limiting of the invention. Accordingly, other objects and advantages of the invention will be apparent to those skilled in the art from the description together with the claims.

I claim:

1. An earthworm collection device wedged within soil comprising:
   a. an applicator having a hand grip wherein the hand grip maintains the applicator securely wedged within the soil, a notched region having a series of equally-spaced notches less than 0.5 inches apart where all the notches are completely within an approximate 10 inch section along its longitudinal axis and having a one-piece tapered end where the tapered end is securely wedged within soil; and b. a striker wherein an approximate right angle interaction between the applicator and the striker generates a vibration that causes the worms to surface.

2. The device of claim 1 wherein said interaction is a repetitive perpendicular stroking motion of the striker along a longitudinal axis of the applicator.

3. The device of claim 1 wherein the applicator is notched on all sides having annular curved crests wherein said notched area prevents disruption in the vibration caused by rotation along the longitudinal axis during use.

4. The device of claim 3 having notches with 0.75 inch width.

5. The device of claim 1 further having a composition selected from the group consisting of aluminum, steel, hardwood, and softwood.

6. The device of claim 1 having a composition of hardwood.

7. The device of claim 1 where the tapered end is approximately 6 inches.

8. The device of claim 1 having an applicator with a diameter of approximately ⅞ inch.

9. The device of claim 1 having notches with a size width selected from the group consisting of 0.25 inch, 0.50 inch, and 0.75 inch.

10. The device of claim 1 wherein the applicator and striker are hollow metal tubes.

11. The device of claim 10 wherein the applicator is a smaller diameter tube than the striker for interlocking storage and transport.

12. A method for collecting earthworms from the surface of soil comprising:

a. penetrating a tapered end of an applicator of claim 1 into the soil wherein the tapered end is securely wedged within the soil;

b. holding the applicator upright while placing a striker of claim 1 perpendicular against a mid-section of the applicator; and c. stroking the striker against a region along a longitudinal axis of the applicator having notches on all sides wherein notches on all sides prevents disruption in the vibration caused by rotation along the longitudinal axis during use and wherein the stroking produces a vibration within the soil to cause the worms to surface.

13. The method of claim 12 wherein penetrating a tapered end of the applicator is approximately 6 inches below the surface of the soil.

14. The method of claim 12 wherein the optimum stroking is approximately 40 strokes per 30 seconds.

15. The method of claim 12 further comprising:

a. picking up the worms before they return under the soil surface; and b. placing them in a container for future use.

16. A kit for collecting earthworms while fishing comprising:

a. a notched hardwood applicator having a hand grip for maintaining the applicator securely wedged within soil, a notched region having a series of equally-spaced notches less than 0.5 inches apart and 0.75 inches wide along the longitudinal axis of the applicator where all the notches are completely within an approximate 10 inch section along its longitudinal axis and having a one-piece tapered end for securely wedging the applicator within the soil; and b. a hardwood striker for generating vibrations along the applicator.

17. The kit of claim 16 having a hardwood applicator having an approximately ⅞ inch diameter.

* * * * *